United States Patent [19]

Koerner et al.

[11] Patent Number: 5,344,949

[45] Date of Patent: Sep. 6, 1994

[54] METHOD FOR THE SYNTHESIS OF SURFACE-ACTIVE ANION-CATION COMPLEXES

[75] Inventors: Götz Koerner, Essen; Klaus-Dieter Klein, Mülheim a.d. Ruhr; Dietmar Schaefer, Hattingen, all of Fed. Rep. of Germany

[73] Assignee: Th. Goldschmidt AG, Essen, Fed. Rep. of Germany

[21] Appl. No.: 92,303

[22] Filed: Jul. 14, 1993

[30] Foreign Application Priority Data

Jul. 22, 1992 [DE] Fed. Rep. of Germany ..... 42241367

[51] Int. Cl.⁵ .......................... C07F 7/08; C07F 7/10
[52] U.S. Cl. .................... 556/413; 556/425; 562/108; 562/114; 554/39; 554/42; 554/46; 554/52; 554/61; 554/68; 554/77; 554/94
[58] Field of Search ............... 556/413, 425; 562/108, 562/114; 554/39, 42, 46, 52, 61, 68, 77, 94

[56] References Cited

U.S. PATENT DOCUMENTS

| | | | |
|---|---|---|---|
| 4,342,742 | 8/1982 | Sebag et al. | 556/419 UX |
| 4,496,705 | 1/1985 | Florence et al. | 556/425 X |
| 4,654,161 | 3/1987 | Kollmeier et al. | 556/419 X |
| 4,891,166 | 1/1990 | Schaefer et al. | 556/419 X |
| 4,895,964 | 1/1990 | Margida | 556/425 |
| 4,898,614 | 2/1990 | Halloran et al. | 556/419 X |
| 4,918,210 | 4/1990 | Fenton et al. | 556/425 |
| 5,041,590 | 8/1991 | Snow | 556/425 |
| 5,068,380 | 11/1991 | Meguriya et al. | 556/413 X |
| 5,073,619 | 12/1991 | O'Lenick | 556/413 X |

*Primary Examiner*—Paul F. Shaver
*Attorney, Agent, or Firm*—Anderson Kill Olick & Oshinsky

[57] ABSTRACT

Surface active anion-cation complexes are synthesized where an organic or organosilicon compound with at least one epoxide group is reacted with a quaternary ammonium hydrogen sulfite of the general formula $$HN^+(R^1)_3 SO_3H^-  \qquad I$$

wherein $R^1$ within the molecule is the same or different and can be (1) an alkyl or hydroxyalkyl group with 1 to 18 carbon atoms, (2) a phenyl group, or (3) a group of the formula $C_nH_{2n+1}CONH-(CH_2)_m-$, in which n can be a number from 7 to 17 and m is 2 or 3, in the presence of a polar solvent in such amounts so that the molar ratio of the epoxide group to $HN^+(R^1)_3SO_3H^-$ is 2:1.

7 Claims, No Drawings

METHOD FOR THE SYNTHESIS OF SURFACE-ACTIVE ANION-CATION COMPLEXES

FIELD OF THE INVENTION

The invention relates to a method for the synthesis of surface active anion-cation complexes. In particular, the invention is directed to a one-step method for the synthesis of surface active anion-cation complexes, in which the anionic and/or cationic component preferably is an organosilicon compound.

BACKGROUND INFORMATION AND PRIOR ART

Anion-cation complexes with surfactant properties, which are essentially independent of the pH, are described in the U.S. Pat. No. 4,093,642. These complexes contain at least one organosilicon compound, which is defined as siloxane A or B.

The siloxane A has the structural formula

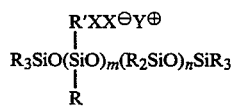

wherein
- R is a univalent hydrocarbon group with 1 to 18 carbon atoms,
- R' is a divalent organic group with 1 to 18 carbon atoms,
- $XX^-$ is a divalent anionic group, which is linked covalently to R' and ionically to $Y^+$,
- $Y^+$ is a univalent cation, which has at least 8 carbon atoms and is derived from a cationic surfactant with a halogen counterion by removal of the halogen and which is free of ionically bound hydrogen,
- m is a whole number with a value of 1 to 100,
- n is a whole number with a value of 0 to 200 and the ratio m/(n+2) amounts to 0.1 to 20.

The siloxane B has the structural formula

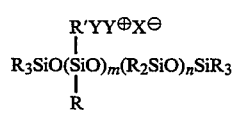

wherein
- R is a univalent hydrocarbon group with 1 to 18 carbon atoms,
- R' is a divalent organic group with 1 to 18 carbon atoms,
- $YY^+$ is a divalent cationic group, which is bound covalently to R' and ionically to $X^-$ and is free of ionically bound hydrogen,
- $X^-$ is a univalent anion, which has at least 8 carbon atoms and is derived from an anionic surfactant with a univalent metal counterion by removal of the metal,
- m is a whole number with a value of 1 to 100,
- n is a whole number with a value of 0 to 200 and the ratio m/(n+2) amounts to 0.1 to 20.

Pursuant to this U.S. Pat. No. 4,093,642, the surface active anion-cation complex is synthesized by first synthesizing the anionic surfactant and the cationic surfactant separately and then mixing equimolar amounts of the two surfactants in a solvent such as water or alcohol and, optionally after removal of the solvent, separating the product from the precipitated salt.

For the case in which the two surfactant components are organosilicon compounds, this reaction can be described as follows.

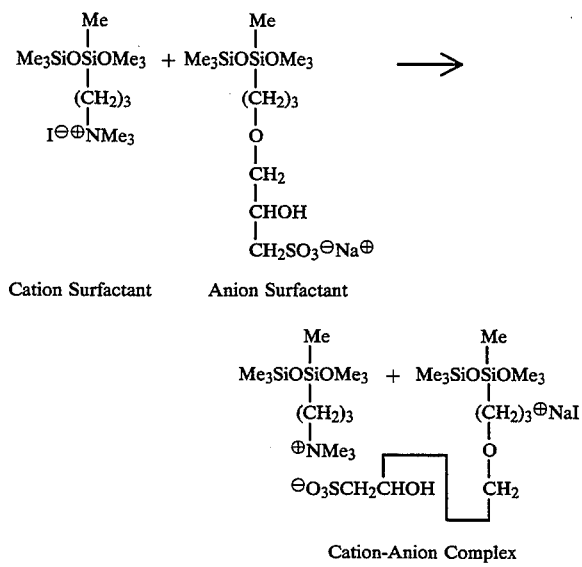

Instead of a silicone surfactant, an organic surfactant can also be selected.

The surfactant complexes have a high surface activity and can be used in manifold ways. It is, however, a disadvantage that, according to this state of the art, it is necessary to employ a 2-step method and to remove a considerable salt load. The method is also unsuitable for synthesizing longer chain and polyfunctional silicone sulfonates and their cation complexes.

The present invention is therefore concerned, in particular, with the simplification of the preparation of such complexes, with the aim of achieving a 1-step method, which can also be employed for longer chain and polyfunctional siloxanes.

OBJECT OF THE INVENTION

An object of the present invention is a method for the synthesis of surface active anion-cation complexes. More particularly, the invention is concerned with a 1-step method for the synthesis of surface active anion-cation complexes, in which the anionic and/or cationic component preferably is an organosilicon compound, with the distinguishing feature that an organic or organosilicon compound with at least one epoxide group is reacted with a quaternary ammonium hydrogen sulfite of the general formula $$HN^+(R^1)_3SO_3H^- \qquad \text{I}$$

wherein
- $R^1$ within the molecule is the same or different and can be
  (1) an alkyl or hydroxyalkyl group with 1 to 18 carbon atoms,
  (2) a phenyl group, or
  (3) a group of the formula $C_nH_{2n+1}CONH-(CH_2)_m-$, in which n can be a number from 7 to 17 and m is 2 or 3, in the presence of a polar solvent in such amounts, that the molar ratio of the epoxide group to $HN^+(R^1)_3SO_3H^-$ is 2:1.

SUMMARY OF THE INVENTION

Chemically, the reaction proceeds in the following manner

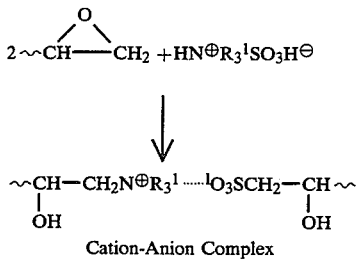

Cation-Anion Complex

No by-products, which have to be removed, are formed by the inventive method.

The inventive method is carried out in the presence of a polar solvent, preferably a low-boiling, aliphatic alcohol, particularly in the presence of isopropanol.

If $R^1$ represents an alkyl or hydroxyalkyl group, the latter can be linear or branched. Preferred are the linear groups, such as the methyl, ethyl, propyl, butyl, hexyl, octyl, decyl, dodecyl or octadecyl group and the corresponding hydroxyalkyl groups. Since the hydrophilicity of the complex decreases as the number of carbon atoms increases, the surfactant properties of the complex can be varied depending on the $R^1$ group selected.

$R^1$ can represent a phenyl group and also a group of the formula $C_nH_{2n+1}CONH\text{—}(CH_2)_m\text{—}$, in which n is a number from 7 to 17 and m is 2 or 3. The $C_nH_{n+1}CO$ group is derived from a fatty acid, such as lauric, palmitic or stearic acid. The acyl group can, however, also be derived from a fatty acid mixture, such as is present in coconut fatty acid.

The $R^1$ groups in the quaternary ammonium hydrogen sulfite can have different meanings. For example, two methyl groups and a $C_{12}H_{25}CONH\text{—}(CH_2)_3\text{—}$ group can be linked to the same nitrogen atom. Further examples of suitable and, at the same time, preferred ammonium hydrogen sulfites are triethylammonium hydrogen sulfite, (2-hydroxyethyl)-dimethylammonium hydrogen sulfite and (2-hydroxypropyl)-dimethylammonium hydrogen sulfite. In principle, however, any combinations are possible so that the $R^1$ group can be selected with a view to the desired application.

Epoxyalkanes are suitable as organic compounds with at least one epoxide group. The carbon chain of the epoxyalkane can be branched. Preferably, compounds of the general formula

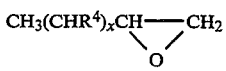

are used as epoxyalkanes, in which $R^4$ represents a hydrogen or an alkyl group with 2 to 6 carbon atoms and can be the same or different within the molecule. If x has a value of 5, $R^4$ can represent, for example, an alkyl group with 2 to 6 carbon atoms once and a hydrogen group four times. The value of x can range from 2 to 14.

Preferably, $R^4$ in the epoxyalkane represents a hydrogen group. In the event that the carbon chain is branched, preferably only one $R^4$ group represents an alkyl group. Particularly preferred compounds are 1,2-epoxyoctane, 1,2-epoxydodecane and 1,2-epoxyhexadecane. As compounds having epoxide groups, it is also possible to use the epoxides of unsaturated fatty acids or their esters. Examples of this are the epoxidized linoleic and linolenic acids and their esters.

Organosilicon compounds with at least one epoxide group correspond, preferably, to the general average formula

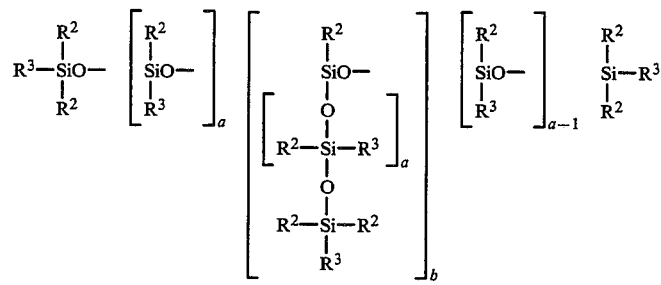

wherein
 $R^2$ in the average molecule is the same or different and represents alkyl groups of 1 to 18 carbon atoms with the proviso that at least 90% of the $R^2$ groups are methyl groups,
 $R^3$ has the same meaning as the $R^2$ group or is an epoxide group linked over a carbon atom to silicon, with the proviso that, in the average molecule, at least one $R^3$ group is an epoxide group,
 a has a value of 0 to 500, and
 b has a value of 0 to 5.

As mentioned above, this formula is an average, general formula. In particular, it indicates the structure units and their number within the molecule. It should, however, be noted that in most cases it is a question of polymeric organosilicon compounds, the chain lengths and degree of branching of which can be different but correspond, on the average, to the values given.

Subscript a has a value of 0 to 500, preferably a value of 1 to 200 and, particularly, a value of 1 to 100.

Subscript b has value of 0 to 5 and preferably of 0 to 3. If b has a value of 0 and a has a value of 1, the organosilicon compound is a modified trisiloxane. The chain length increases as the value of a increases and the degree of branching increases as the value of b increases.

At least one $R^3$ group in Formula II must represent an epoxide group. Preferred examples of suitable epoxide groups have the following formulas.

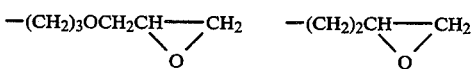

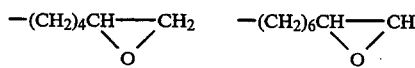 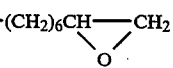
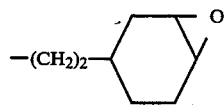 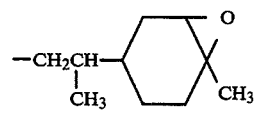
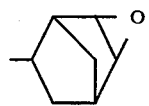 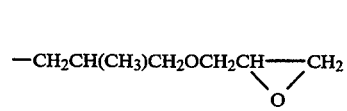
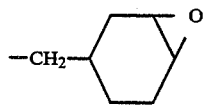

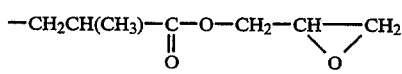

The inventive method can be carried out by reacting an organosilicon compound of Formula II or a mixture of such compounds with the quaternary ammonium hydrogen sulfite or by using a mixture of organosilicon compounds of Formula II and organic compounds with, in each case, at least one epoxide group.

Preferably, organosilicon compounds of Formula II are used as the compound with at least one epoxide group. It is, however, possible to influence the properties of the surface active anion-cation complex by the simultaneous presence of organic compounds with at least one epoxide group.

Examples of surface active anion-cation complexes, synthesized pursuant to the invention, are

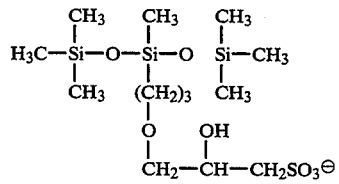

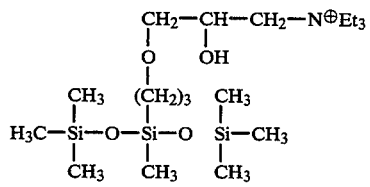

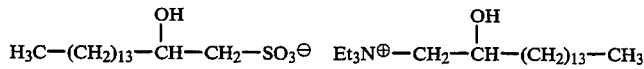

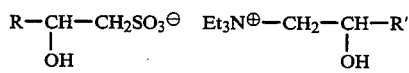

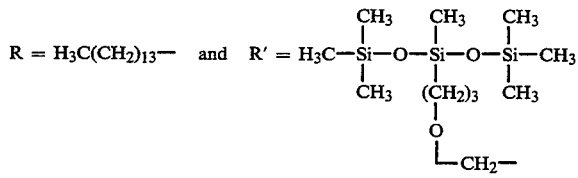

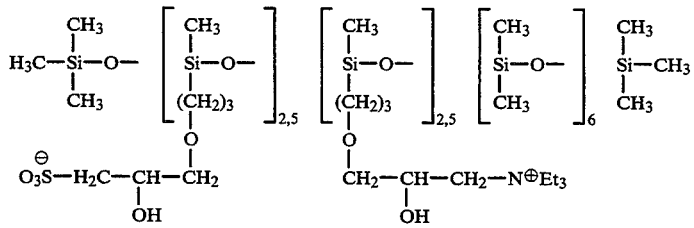

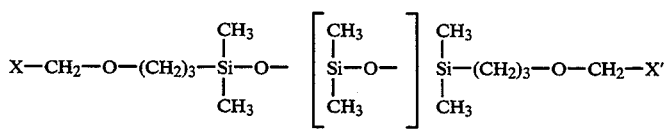

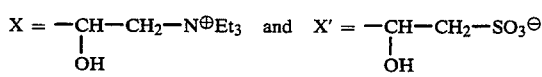

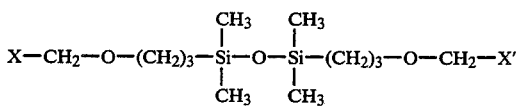

X and X' being defined as above

The complexes, synthesized pursuant to the invention, are distinguished by a low critical micelle concentration [cmc]. Viscous, clear liquids are obtained from the reaction of organopolysiloxanes modified with epoxides. As the addition of alkane epoxides to the reaction mixture increases, waxy solids with defined melting points are obtained, depending on the length of the alkyl chain.

The properties of the anion-cation complexes, synthesized pursuant to the invention, depend in a manner known to the expert on the nature of the educts chosen. If the backbone of the polysiloxane is a short chain, the typical properties of a wetting agent predominate. As the molecular weight increases and, optionally, with the use of alkane epoxides, the relative compatibility of these products with plastics increases. The products then develop antistatic, lubricating or also releasing properties. The complexes, synthesized pursuant to the invention, can also be used as emulsifiers, particularly for the preparation of W/O emulsions.

In the following Examples 2 to 12, the inventive method is described in greater detail and the application properties of the products are shown. Example 1 describes the synthesis of the quaternary ammonium hydrogen sulfite used in the reaction. This synthesis is carried out in a known manner. Example 1 therefore is not of the invention. It is understood that the examples are given by way of illustration and not by way of limitation.

EXAMPLE 1

(Not of the invention)

Synthesis of Triethylammonium Hydrogen Sulfite by Known Methods

Triethylamine (101.19 g, 1 mole), 18.0 g (1 mole) of water and 200.0 g of isopropanol are mixed with stirring in a 500 mL 3-neck flask, which is provided with reflux condenser, stirrer, gas-inlet tube and internal thermometer. Sulfur dioxide is then passed in at room temperature, the internal temperature rising up to 42° C. After the exothermic reaction declines, the passing in of the gas is stopped and the sulfur dioxide uptake is determined by weighing after nitrogen has been passed through the reaction mixture.

Theoretically: 64.0 g increase in weight; actually: 64.3 g

The product is used without being worked up further. (2-Hydroxypropyl)-dimethylammonium hydrogen sulfite and (2-hydroxyethyl)-dimethyl hydrogen sulfite are synthesized in the same way.

Synthesis of the Inventive Compounds

EXAMPLE 2

Reaction of 3-(Glycidyloxypropyl)-1,1,1,3,5,5,5-heptamethyl-trisiloxane with Triethylammonium Hydrogen Sulfite In a 2 L 3-neck flask, equipped with stirrer, reflux condenser and dropping funnel, 627.4 g (2 equivalents) of 3-(glycidyloxypropyl)-1,1,1,3,5,5,5-heptamethyltrisiloxane are added dropwise to 183.5 g (1 mole) of triethylammonium hydrogen sulfite dissolved in 200.0 g of isopropanol at an internal temperature of 30° C. Stirring is then continued for 1 hour, the reaction mixture becoming clear. Subsequently, the reaction mixture is heated for 6 hours at the refluxing temperature.

After cooling, 1% by weight of bentonite is mixed in as filter and the reaction mixture is filtered. The product is then freed from volatile components under the vacuum of an oil pump at a water bath temperature of 80° C.

A waterwhite, viscous product, with a Brookfield viscosity of 18,850 mPa×sec at 24° C., is obtained, which forms a cloudy solution in water.

The 1% solution in distilled water has a surface tension of 20.7 mN/m and a spreading value of 65 mm on a polypropylene plate. Analytical investigations by means of $^1$H and $^{13}$C NMR spectroscopy confirm that the reaction product has the expected structure, as follows:

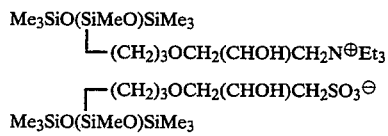

The product is miscible with a hydroxy-functional polydimethylsiloxane with an average chain length of 50 (referred to hereinafter as HPDM). It can be prepared without. problems as a 5% (in a surfactant) mixture, which remains stable after being kept for 12 hours at 40° C. Furthermore, the product is soluble in silicone oil that has a viscosity of 100 mPa×sec to form a cloudy solution. A 5% solution separates after being kept for 12 hours at 40° C.

The surfactant sulfur content analysis of the product makes it clear that an ion associate is present. Measurements at a pH of 3, 5 and 7 reveal no surfactant sulfur.

Elementary analysis of the reaction product reveals the following (element/actual/theoretical): N/1.6%/1.7%; C/45.3%/46.6%; H/9.3%/9.8%; S/3.9%/3.9%; Si/17.4%/20.4%; O/not calculated.

As indicated below, measurements of aqueous solutions of this substance, even at low concentrations, show excellent surface activity, which is expressed in a particularly effective lowering of the surface tension.

| Concentration (% by weight) | Surface Tension (mN/m) (T = 25° C.) |
| --- | --- |
| 1.0 | 20.7 |
| 0.03 | 20.9 |
| 0.01 | 20.9 |
| 0.007 | 21.0 |
| 0.002 | 23.4 |
| 0.001 | 25.6 |

EXAMPLE 3

Reaction of 3-(Glycidyloxypropyl)-1,1,1,3,5,5,5-heptamethyl-trisiloxane with (2-Hydroxypropyl)-dimethylammonium Hydrogen Sulfite The preparation is carried out as already described in Example 2, using 51.58 g (0.5 moles) of (2-hydroxypropyl)-dimethylammonium hydrogen sulfite, dissolved in 100 g of isopropanol, and 313.9 g (1 equivalent) of 3-(glycidyloxypropyl)-1,1,1,3,5,5,5-heptamethyltrisiloxane.

After the reaction product is worked up, a viscous, yellowish liquid, with a viscosity of 170,000 mPa×sec at 23° C., is obtained, which forms a milky solution in water, a cloudy solution in silicone oil and a clear solution in HPDM. The solutions are stable even after being kept for 12 hours at 40° C. A 1% solution in distilled water has a surface tension of 21.0 mN/m and a spreading value of 45 mm on polypropylene.

EXAMPLE 4

Reaction of 3-(Glycidyloxypropyl)-1,1,1,3,5,5,5-heptamethyl-trisiloxane with (2-Hydroxyethyl)-dimethylammonium Hydrogen Sulfite The reaction is carried out as described in Example 2, using 44.57 g (0.5 moles) of (2-hydroxyethyl)-dimethylammonium hydrogen sulfite and 313.9 g (1 equivalent) of 3-(glycidyloxypropyl)-1,1,1,3,5,5,5-heptamethyltrisiloxane.

Here also, a highly viscous, clear, yellowish product, with a viscosity of 79,000 mPa×sec at 23° C., is obtained, which dissolves in water to form a clear solution. It is furthermore soluble in silicone oil (100 mPa×sec) forming a cloudy solution and in HPDM forming a clear solution. No phase separation can be detected even after being kept for 12 hours at 40° C. The 1% aqueous solution has a surface tension of 21.3 mN/m and a spreading value of 50 mm on polypropylene.

EXAMPLE 5

Reaction of an α,-di-(Glycidyloxypropyl)polydimethylsiloxane Having an Average Chain Length of 38 Silicon Atoms with Triethylammonium Hydrogen Sulfite The procedure is as described for Example 2, 45.9 g (0.25 moles) of triethylammonium hydrogen sulfite, dissolved in 100 mL of isopropanol, and 761.9 g (0.5 equivalents) of α,-di-(glycidyloxypropyl)polydimethylsiloxane with an average chain length of 38 silicon atoms being used.

A clear colorless product is obtained, which has a viscosity of 11,000 mPa×sec at 22° C. and is not readily soluble in water. A 1% aqueous solution has a surface tension of 49.5 mN/m and a spreading value of 7 mm on polypropylene. The product forms a clear solution in a silicone oil having a viscosity of 100 mPa×sec and also in HPDM (5%); the solution is stable even after having been kept for 12 hours at 40° C.

EXAMPLE 6

Reaction of a Polydimethylsiloxane Having an Average Chain Length of 13 Silicon Atoms and 5 Lateral Glycidyloxypropyl Groups with Triethylammonium Sulfite The procedure is as described for Example 2, 45.9 g (0.25 moles) of triethylammonium hydrogen sulfite, dissolved in 100 mL of isopropanol, and 202 g (0.5 equivalents) of the above-described epoxy-functional polydimethylsiloxane being used.

A clear colorless product is obtained, which has a viscosity of 655,000 mPa×sec at 22° C. and forms a cloudy solution in water, silicone oil (with a viscosity of 100 mPa×sec) and in HPDM; these solutions remain stable even after having been kept for 12 hours at 40° C.

The 1% aqueous solution has a surface tension of 22.4 mN/m and a spreading value of 6 mm (polypropylene sheet, no spreading).

EXAMPLE 7

Reaction of a Polydimethylsiloxane Having an Average Chain Length of 13 Silicon Atoms, 5 Lateral and 2 Terminal Glycidyloxypropyl Groups with Triethylammonium Hydrogen Sulfite Similarly, 45.9 g (0.25 moles) of triethylammonium hydrogen sulfite, dissolved in 100 mL of isopropanol, are reacted with the epoxy functional polydimethylsiloxane described in greater detail above.

The viscous, clear product, the viscosity of which is not measurable at 24° C., dissolves in silicone oil (with a viscosity of 100 mPa×sec) and in HPDM to form a cloudy solution. Both solutions separate after having been kept for 12 hours at 21° C. or 40° C.

A 1% solution in water has a surface tension of 24.7 mN/m and a spreading value of 6 mm (no spreading).

EXAMPLE 8

Reaction of 1,3-Di(glycidyloxypropyl)-1,1,3,3-Tetramethyldisiloxane with Triethylammonium Hydrogen Sulfite Amounts used: 91.8 g (0.5 moles) of triethylammonium hydrogen sulfite and 190.5 g (1 equivalent) of the 1,2-diepoxydisiloxane described in greater detail above.

The product, the viscosity of which is not measurable at 23° C., shows in HPDM as well as in a silicone oil having a viscosity of 100 mPa×sec the same solubility behavior described in Example 7.

The surface tension of a 1% aqueous solution is 23.7 mN/m and the spreading value is 12 mm.

EXAMPLE 9

Reaction of 1,2-epoxyoctane with Triethylammonium Hydrogen Sulfite

Amounts used: 183.5 g (1 mole) of triethylammonium hydrogen sulfite, dissolved in 100 mL of isopropanol, and 246.46 g (2 moles) of 1,2-epoxyoctane. The components can be reacted without additional solvent variation as described in Example 2.

A clear, colorless liquid, with a viscosity of 5,800 mPa×sec at 23° C. is obtained. The substance is soluble in water, silicone oil and HPDM forming cloudy solutions. A phase separation can be detected in the two solutions mentioned last after these have been kept for 12 hours at 40° C. A 1% solution in water does not spread on polypropylene sheet; the surface tension, however is lowered to 27 mN/m.

EXAMPLE 10

Reaction of 1,2-Epoxyhexadecane with Triethylammonium Hydrogen Sulfite

Amounts used: 183.5 g (1 mole) of triethylammonium hydrogen sulfite, dissolved in 100 mL of isopropanol, and 480.86 g (2 moles) of 1,2-epoxyhexadecane. The components can also be reacted here without additional solvent variation as described in Example 2.

A white, waxy solid with a melting point of 44° C. is obtained. The surface tension of the 1% aqueous solution is 28.2 mN/m (cloudy solution). Spreading (7 mm) cannot be observed.

The substance is not soluble in silicone oil that has a viscosity of 100 mPa×sec and forms a cloudy solution in HPDM.

EXAMPLE 11

Reaction of 1,2-epoxyoctane and 3-(glycidyloxypropyl)-1,1,1,3,5,5,5-heptamethylsiloxane with Triethylammonium Hydrogen Sulfite Amounts used: 183.5 g (1 mole) triethylammonium hydrogen sulfite, dissolved in 100 mL of isopropanol, 123.23 g (1 mole) of 1,2-epoxyoctane and 313.9 g (1 equivalent) of 3-(glycidyloxypropyl)-1,1,1,3,5,5,5-heptamethyltrisiloxane.

A clear, colorless liquid with a viscosity of 6,200 mPa×sec at 23° C. is obtained. It forms a cloudy solution in water and silicone oil and is readily soluble in HPDM. The solutions in silicone oil and HPDM remain stable even after having been kept for 12 hours at 40° C.

The spreading value of a 1% solution is 35 mm and the surface tension is 20.7 mN/m.

EXAMPLE 12

Reaction of 1,2-epoxyhexadecane and 3-(glycidyloxypropyl)-1,1,1,3,5,5,5-heptamethyltrisiloxane with Triethylammonium Hydrogen Sulfite Amounts used: 183.5 g (1 mole) of triethylammonium hydrogen sulfite, dissolved in 100 mL of isopropanol, 240.43 g (1 mole) of 1,2-epoxyhexadecane and 313.9 g (1 equivalent) of 3-(glycidyloxypropyl)-1,1,1,3,5,5,5-heptamethyltrisiloxane.

A white pasty mass is obtained, which liquifies at about 50° C., remaining somewhat cloudy.

It is incompletely soluble in water and insoluble in silicone oil having a viscosity of 100 mPa×sec and forms a cloudy solution in HPDM. The cloudy solution in HPDM is stable even after having been kept for 12 hours at 40° C.

The 1% aqueous solution has a surface tension of 22.3 mN/m and a spreading value of 33 mm on a polypropylene sheet.

We claim:

1. A method for the synthesis of surface active anion-cation complexes comprising the steps of reacting an organic or organosilicon compound having at least one epoxide group, wherein said organic compound is of the general formula $$CH_3(CHR^4)_x-CH\underset{O}{-\!-\!-}CH_2$$

Wherein $R^4$ is a hydrogen or alkyl group with 2 to 6 carbon atronis and X is a number from 2 to 14, or the organic compound is an epoxide of an unsaturated fatty acid or its ester, with a quaternary ammonium hydrogen sulfide of the general formula $$HN^+(R^1)_3SO_3H \qquad I$$

wherein $R^1$ within a molecule is the same or different and can be
 (1) an alkyl or hydroxyalkyl group with 1 to 18 carbon atoms;
 (2) a phenyl group; or
 (3) a group of the formula $C_nH_{2n+1}COHN-(CH_2)_m-$, in which n can be a number from 7 to 17 and m is 2 or 3;

in the presence of a polar solvent in such amount that the molar ratio of the epoxide group to $HN^+(R^1)_3SO_3H$ is about 2:1.

2. The method of claim 1, further comprising as organosilicon compound having at least one epoxide group, a compound of the average general formula $$R^3-\underset{\underset{R^2}{|}}{\overset{\overset{R^2}{|}}{Si}}O-\left[\underset{\underset{R^3}{|}}{\overset{\overset{R^2}{|}}{Si}}O-\right]_a\left[\underset{\underset{\underset{\underset{R^3}{|}}{Si-R^2}}{\overset{O}{|}}}{\overset{\overset{R^2}{|}}{Si}O-}\right]_b\left[\underset{\underset{R^3}{|}}{\overset{\overset{R^2}{|}}{Si}O-}\right]_{a-1}\underset{\underset{R^2}{|}}{\overset{\overset{R^2}{|}}{Si}}-R^3$$

is used, wherein $R^2$ in an average molecule is the same or different and represents alkyl groups of 1 to 18 carbon atoms with the proviso that at least 90% of the groups are methyl groups;

$R^3$ has the same meaning as the $R^2$ group or is an epoxide group linked over a carbon atom to silicon, with the proviso that, in an average molecule, at least one $R^3$ group is an epoxide group;

a has a value of 0 to 500; and b has a value of 0 to 5.

3. The method of claim 2, comprising compounds that are used having at least one $R^3$ as an epoxide group selected from the group having the formulas

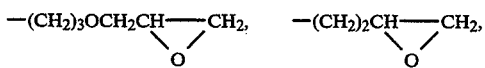
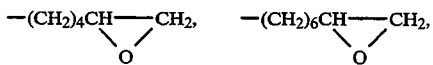
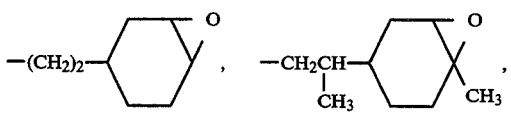
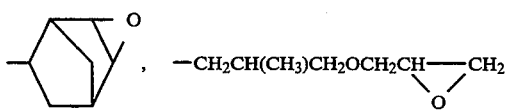

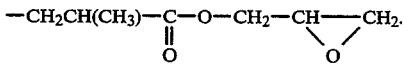

4. The method of claim 1, comprising that the mixture of different organosilicon compounds or mixture of organosilicon and organic compounds used having, in each case, at least one epoxide group.

5. The method of claim 1 comprising that the solvent used is low-boiling aliphatic alcohol.

6. The method of claim 5, further comprising that the solvent used is isopropanol.

7. A surface active anion-cation complex obtained by the method of claim 1.

* * * * *